US006582442B2

(12) United States Patent
Simon et al.

(10) Patent No.: US 6,582,442 B2
(45) **Date of Patent: *Jun. 24, 2003**

(54) METHOD AND SYSTEM FOR PERFORMING MICROABRASION

(75) Inventors: Eric M. Simon, Salt Lake City, UT (US); Randall D. Block, Salt Lake City, UT (US)

(73) Assignee: Dynatronics Corporation, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,531

(22) Filed: Feb. 28, 2000

(65) Prior Publication Data

US 2002/0169461 A1 Nov. 14, 2002

(51) Int. Cl.[7] .......... A61B 17/50

(52) U.S. Cl. .......... 606/131; 606/167

(58) Field of Search .......... 606/131, 133, 606/167; 604/289, 290, 310; 451/53, 87

(56) References Cited

U.S. PATENT DOCUMENTS

| | | | | |
|---|---|---|---|---|
| 554,299 A | 2/1896 | Parker | |
| 2,238,541 A | 4/1941 | Spagnolo | 15/14 |
| 2,608,032 A | 8/1952 | Garver | 51/11 |
| 2,921,585 A | 1/1960 | Schumann | 128/355 |
| 3,085,573 A | 4/1963 | Meyer et al. | 128/240 |
| 3,297,024 A | 1/1967 | Robinson | 128/38 |
| 3,543,444 A | * 12/1970 | Mehta | 451/53 |
| 3,574,239 A | 4/1971 | Sollerud | 4/1 |
| 3,715,838 A | 2/1973 | Young et al. | 51/12 |

(List continued on next page.)

FOREIGN PATENT DOCUMENTS

| | | |
|---|---|---|
| DE | 532 086 | 8/1931 |
| DE | 201229 | 12/1958 |
| DE | 2 218 370 | 9/1973 |

(List continued on next page.)

OTHER PUBLICATIONS

BHC Group web page, "Dermabraze," Jun. 1999, http://www.bhc–group.demon.co.uk/dermabra,html.
Dynatronics Corporation product brochure, "Synergie Lifestyle System" Salt Lake City, Utah 1998.
Dynatronics Corporation product brochure, "Synergie The Ultimate Cellulite Solution" Salt Lake City, Utah 1999.

(List continued on next page.)

*Primary Examiner*—Pedro Philogene
(74) *Attorney, Agent, or Firm*—Kirton & McConkie; Berne S. Broadbent

(57) ABSTRACT

A method and system for performing abrasion on a surface, such as on the skin of a patient, is disclosed. The dermabrasion apparatus includes apparatus for delivering and retrieving material to and from a selected site to be abraded, a delivery and retrieval hand piece, an abrasive handling device, and a waste retrieval holding device. The hand piece is coupled to the abrasive handling device as well as the waste retrieval holding device, which is further coupled to the delivery and retrieval apparatus. The abrasive handling device further includes an abrasive supply device, a receiving channel, a feeding chamber, and a delivery channel. The abrasive supply device typically is a canister fitted with a funnel-shaped spout that is inverted into the receiving channel. The receiving channel feeds abrasive to the feeding chamber. The delivery and retrieval apparatus, typically a vacuum source that generates a pneumatic air supply within the abrasion apparatus, causes the abrasive within the feeding chamber to loft in an arc such that it reaches the delivery channel. The delivery channel then leads to the hand piece, which is utilized to apply the abrasive to the surface and then retrieve the waste debris during the procedure.

21 Claims, 6 Drawing Sheets

U.S. PATENT DOCUMENTS

| | | | | | |
|---|---|---|---|---|---|
| 3,760,800 | A | | 9/1973 | Staffin et al. | 128/24.1 |
| 3,841,322 | A | | 10/1974 | Spelio | 128/40 |
| 3,841,323 | A | | 10/1974 | Stoughton | 128/40 |
| 4,090,334 | A | | 5/1978 | Kurowski et al. | 51/427 |
| 4,214,576 | A | | 7/1980 | Henley | 128/24.1 |
| 4,333,277 | A | * | 6/1982 | Tasedan | 451/101 |
| 4,375,740 | A | | 3/1983 | Brown | 51/425 |
| 4,445,517 | A | | 5/1984 | Feild | 128/752 |
| 4,498,462 | A | | 2/1985 | Henley | 128/24.1 |
| 4,516,398 | A | | 5/1985 | Wuchinich | 604/22 |
| 4,531,934 | A | | 7/1985 | Kossovsky et al. | 604/22 |
| 4,560,373 | A | | 12/1985 | Sugino et al. | 604/30 |
| 4,578,058 | A | | 3/1986 | Grandon | 604/27 |
| 4,583,530 | A | | 4/1986 | Henley | 128/65 |
| 4,646,480 | A | | 3/1987 | Williams | 51/424 |
| 4,674,239 | A | | 6/1987 | Jodoin | 51/424 |
| 4,676,749 | A | | 6/1987 | Mabille | 433/88 |
| 4,729,368 | A | | 3/1988 | Guitay | 128/57 |
| 4,757,814 | A | | 7/1988 | Wang et al. | 128/318 |
| 4,883,047 | A | | 11/1989 | Guitay | 128/38 |
| 4,966,609 | A | | 10/1990 | Callinan et al. | 51/295 |
| 5,037,431 | A | | 8/1991 | Summers et al. | 606/131 |
| 5,037,432 | A | * | 8/1991 | Molinari | 606/131 |
| 5,080,656 | A | | 1/1992 | Martz et al. | 604/289 |
| 5,100,412 | A | * | 3/1992 | Rosso | 451/53 |
| 5,152,281 | A | | 10/1992 | Koll | 128/57 |
| 5,207,234 | A | | 5/1993 | Rosso | 128/898 |
| 5,215,078 | A | | 6/1993 | Fulop | 128/52 |
| 5,322,504 | A | | 6/1994 | Doherty et al. | 606/167 |
| 5,330,354 | A | * | 7/1994 | Gallant | 451/87 |
| 5,334,016 | A | | 8/1994 | Goldsmith et al. | 433/29 |
| 5,334,019 | A | | 8/1994 | Goldsmith et al. | 433/88 |
| 5,350,299 | A | | 9/1994 | Gallant | 433/88 |
| 5,423,803 | A | | 6/1995 | Tankovich et al. | 606/9 |
| 5,484,283 | A | | 1/1996 | Franetzki | 433/116 |
| 5,489,291 | A | | 2/1996 | Wiley | 606/170 |
| 5,525,058 | A | | 6/1996 | Gallant et al. | 433/88 |
| 5,562,643 | A | | 10/1996 | Johnson | 604/290 |
| 5,665,053 | A | | 9/1997 | Jacobs | 601/2 |
| 5,681,026 | A | | 10/1997 | Durand | 251/129.16 |
| 5,752,829 | A | * | 5/1998 | Goldsmith et al. | 451/87 |
| 5,765,759 | A | | 6/1998 | Bruns et al. | 239/398 |
| 5,795,626 | A | | 8/1998 | Gabel et al. | 427/458 |
| 5,800,446 | A | | 9/1998 | Banuchi | 606/131 |
| 5,810,842 | A | * | 9/1998 | Di Fiore et al. | 606/131 |
| 5,885,211 | A | | 3/1999 | Eppstein et al. | 600/309 |
| 5,971,999 | A | | 10/1999 | Naldoni | 606/131 |
| 6,012,975 | A | * | 1/2000 | Jager | 451/87 |
| 6,139,554 | A | | 10/2000 | Karkar et al. | 606/131 |
| D441,863 | S | | 5/2001 | Khalaj et al. | D24/133 |
| 6,235,039 | B1 | * | 5/2001 | Parkin et al. | 606/131 |
| 6,241,739 | B1 | | 6/2001 | Waldron | 606/131 |

FOREIGN PATENT DOCUMENTS

| | | | | | |
|---|---|---|---|---|---|
| DE | 2742058 | A1 | | 3/1979 | |
| DE | 3421390 | A1 | | 12/1985 | |
| DE | 234608 | A1 | | 4/1986 | |
| DE | 3535 571 | A1 | | 5/1987 | |
| DE | 4102684 | A1 | | 8/1992 | |
| DE | 9215436 | | | 3/1994 | |
| EP | 0035040 | A1 | | 9/1981 | |
| EP | 0143617 | A2 | | 6/1985 | |
| EP | 0258901 | A2 | | 3/1988 | |
| EP | 0564392 | A2 | | 10/1993 | |
| EP | 0806184 | A1 | | 11/1997 | |
| FR | 638 309 | | | 5/1928 | |
| FR | 1.109.131 | | | 1/1956 | |
| FR | 1109131 | | * | 1/1956 | 601/6 |
| FR | 1.136.127 | | | 5/1957 | |
| FR | 1.501.054 | | | 11/1967 | |
| FR | 2.057.514 | | | 5/1971 | |
| IT | 553076 | | | 12/1956 | |
| IT | 1184922 | | | 10/1987 | |
| NO | 50247 | | | 2/1932 | |
| RU | 1556676 | A1 | | 4/1990 | |
| SE | 168 279 | | | 6/1934 | |
| SE | 152 189 | | | 11/1955 | |
| WO | WO 96/03959 | | | 2/1996 | |
| WO | WO 97/11650 | | | 4/1997 | |
| WO | WO 99/07439 | | | 2/1999 | |
| WO | WO 99/20336 | | | 4/1999 | |
| WO | WO 99/23951 | | | 5/1999 | |
| WO | WO 00/67692 | | | 11/2000 | |

OTHER PUBLICATIONS

Optical Technology, Inc. web page, "Derma Genesis," Jul. 1999, http://www.dermagenesis.com/main.html.

Pneumadyne web page, "Introducing the New Bleed Valve," Dec. 1998, http://www.pneumadyne.com/c–products/bleed.html.

Soundskin Corporation product brochure, "Smart Peel Skin Exfoliation System," 1998.

English language translation for German Patent No. 2 218 370, attached to the back of the patent.

English language abstract for German Patent No. 3535 571 A1, attached to the front of the patent.

English language translation for Swiss Patent No. 168 279, attached to the back of the patent.

English language abstract for Russian Patent No. 1556676 A1, attached to the front of the patent.

English language abstract for PCT Patent No. WO96/03959, attached to the front of the patent.

English language abstract for German Patent No. DE 4102684 A1, listed above.

English language abstract for German Patent No. DD 234608 A1, listed above.

English language abstract for German Patent No. DE 3421390 A1, listed above.

SoundSkin Corporation, "Smart Peel Skin Exfoliation System" (1998, U.S.A.).

* cited by examiner

METHOD AND SYSTEM FOR PERFORMING MICROABRASION

RELATED APPLICATIONS

This patent application is related to commonly assigned U.S. Design patent application Ser. No. 29/119,496, entitled DERMABRASION SYSTEM, and to U.S. Design patent application Ser. No. 29/119,377, entitled DERMABRASION HAND PIECE, both filed even date herewith and incorporated by reference for all purposes.

THE BACKGROUND OF THE INVENTION

The present invention relates generally to abrasion systems and methods for abrading a surface in a controlled manner and, more particularly, to a portable or adaptable microabrasion system that operates to perform dermabrasion in a controlled manner with improved efficiency, hygiene, and finish.

Microdermabrasion techniques and systems are well known to those skilled in the art. A typical dermabrasion system includes a pneumatic drive such as either a negative pressure system or a positive pressure system, that delivers an ablative material from a supply point to a hand piece, also known as a wand, which has a small aperture to be placed upon a patient's skin during the abrasion process. In the negative pressure system, such as one utilizing a vacuum for pneumatic drive, the closing of the aperture by the skin completes the pneumatic circuit drawing the abrasive material to the skin to perform dermabrasion. The refuse and debris after the abrasive procedure is vacuumed away into a waste storage container for disposal.

Each stage of operation within current dermabrasion systems suffer problems that prevent optimal and efficient operation on a subject or patient. One problem is the handling of the abrasive material at the supply point. Typical supply points utilize abrasive supply containers that are permanently mounted and must be refilled when empty. These containers are usually difficult to access and lead to waste and unnecessary exposure to the abrasive material during filling. Further, due to the dynamics of the content level changing, the systems fail to deliver consistent amounts of abrasive material from the supply containers to the hand piece. As such, the results of the abrasive operation are inconsistent and vary in the length of time normally needed to perform an typically procedure/session. As the container goes from full to empty, performance can suffer severely, with as much as a 75% reduction in abrasive concentration in the air stream. Additionally, few, if any, systems are able to utilize all the contents of the supply container before needing refilling.

An additional problem with current supply containers is that they draw upon ambient air. Ambient air is often humid and the moisture therein causes the moisture-sensitive abrasive to agglomerate and subsequently clog the system. This is especially a problem in that most systems utilize a small output aperture that clogs easily, particularly when the abrasive material becomes damp with humidity, leading to clumping and clogging and generally inconsistent delivery of abrasive. Often, the existing systems are induced to employ mechanical or pneumatic means, such as spring-loaded rods or compressed air, to periodically clear the restricted output aperture.

Another part of the abrasive delivery system is an abrasive/concentration control system. Most systems lack such a control system. The control system's purpose is to control the amount of abrasive delivered to the hand piece during operation. Some systems utilize an electronic control that causes pulses resulting in pressure surges and non-uniform delivery of the abrasive. Other systems utilize control systems that are difficult to adjust, hard to reset and fail to provide repeatable consistent results for subsequent treatments.

The hand piece is a critical component of any dermabrasion system. Hand pieces suffer several problems. One problem is that the apertures tend to restrict the flow of the abrasive material to the skin as well as hinder removal of the abraded material and the abrasive during the abrasion procedure. Further, the dermabrasion procedure involves removal of skin and sometimes blood, so there is concern that the use of the same wand from patient to patient is unsanitary and unhealthy. Attempts to make the hand piece more hygienic by having disposable and replaceable wand tips has been unsuccessful as the tips merely prevent contamination at the aperture level without addressing a problem known as back contamination, which occurs when refuse debris within the wand from a previous procedure contaminates the wand tip in spite of the replacement of a fresh tip.

Further, some hand pieces are designed without thought about how the hand piece is to be cleaned. As such, these pieces are difficult to clean and therefore, undesirable for long term use. Also, most hand pieces are expensive to manufacture. They can be heavy and awkward to use, such that the technician suffers discomfort and fatigue during long sessions or over several sessions during the same day. Since the piece needs to be small enough to handle, they often have restricted flow paths that detrimentally affect flow rate and delivery of the abrasive for optimal results and for quick pick up of the waste debris.

Another element of the dermabrasion system includes a waste recovery or accumulation container system. Most systems are permanently mounted and are difficult to access, empty, and clean. The containers collect abrasive dust along with skin cells, and bodily fluids, which may contain microbes or other undesirable elements. As such, the containers must be emptied and cleaned periodically. Failure to clean the container can result in unwanted growths and other hazardous health risks that should be avoided at all times.

The waste accumulation systems often have small exhaust apertures that can easily clog with waste products resulting in restricted air flow within the overall system. Moreover, filter elements are also employed to prevent abrasive and debris out flow into the vacuum source. Such filters are a major source of clogging and reduction of optimal air flow within the entire system, thereby leading to poor dermabrasion results since less abrasive material is being carried within the system at a reduced speed. Similar to the supply system, one solution has been to use back pressure to clear and clean the filters or unplug the clogs in the waste accumulation system, but this adds cost and complexity to the overall design, which can result in mechanical failure, decreased abrasion performance, and increased costs of production and operation.

Accordingly, what is needed is a dermabrasion system and method that overcomes the problems of the prior art. Specifically, what is needed is a dermabrasion system that controls the dispersion of the abrasive material over the entire range of operation uniformly and consistently over the prior art methods. Further, what is needed is a method and system for handling the abrasive material prior to the ablative operation and afterwards during the collection of the contaminated materials. Further still what is needed is a hand piece that is lightweight and easily cleaned to meet high health safety standards, yet allows for high air flow.

SUMMARY OF THE INVENTION

According to the present invention, a method and system for performing abrasion on a surface, such as on the skin of a patient, is disclosed. The dermabrasion apparatus includes means for delivering and retrieving material to and from a selected site to be abraded, a delivery and retrieval hand piece, an abrasive handling device, and a waste retrieval holding device. The hand piece is coupled to the abrasive handling device as well as the waste retrieval holding device, which is further coupled to the delivery and retrieval means. The abrasive handling device further includes an abrasive supply device, a receiving channel, a feeding chamber, and a delivery channel. The abrasive supply device typically is a canister fitted with a funnel-shaped spout that is inverted into the receiving channel. The receiving channel feeds abrasive to the feeding chamber. The delivery and retrieval means, typically a vacuum source that generates a pneumatic air supply within the abrasion apparatus, causes the abrasive within the feeding-chamber to loft in an arc such that it reaches the delivery channel. The abrasive travels through the delivery channel under pressure to the hand piece, which is utilized to apply the abrasive to the surface and then retrieve the waste debris from the procedure. The abrasion apparatus may also include a massage or body contouring system, which also utilizes the vacuum source.

Further, the receiving channel extends within the feeding chamber and serves to limit or control the amount of abrasive filling the feeding chamber. The receiving chamber's height, relative to its location within the feeding chamber, can be adjusted by way of an height adjustment means. The feeding chamber typically comprises top and bottom portions as well as generally sloped side walls that slope inwardly from the top to the bottom. Such geometries lend themselves to the shapes including funnels, inverted pyramids, bowl shapes, and other geometries where the walls are sloped in such a fashion so that the abrasives accumulate in a concentrated point at the bottom. Placed between the supply device and the feeding channel is an additional chamber that provides for the abrasive to feed within the receiving channel without blocking the insertion of the funnel within the supply device. The feeding chamber is further coupled to an ambient air supply with a filter interspersed between ambient and the feeding chamber to prevent unwanted matter from being drawn within the apparatus as well as to prevent abrasive from spilling out an open aperture where the ambient port is located.

The dermabrasion hand piece comprises a body having a first end, a second end, a delivery channel, and a retrieval channel. The delivery channel extends the length of the body and the retrieval channel is concentric with the delivery channel, but has a larger diameter. A delivery aperture is located at the first end of the body. A retrieval aperture is placed adjacent and generally concentric with the delivery aperture. The delivery aperture is coupled to the delivery channel while the retrieval aperture is coupled to the retrieval channel. The dermabrasion hand piece further includes a dermabrasion tip that has a first end, which is removably mounted to the first end of the body, a second end, and a delivery aperture in the second end. The delivery aperture is generally concentric with the delivery channel and the delivery aperture. The tip is generally dome shaped and is made from a high density plastic or metal to withstand the abrading effects of the abrasive during operation. At the second end of the body are located an intake aperture and an outlet aperture. The intake aperture is concentric with the delivery channel while the outlet aperture is connected to the retrieval channel and is offset from the intake aperture.

The body may be further comprised of two portions, a body section and an end portion. Inserted between the end portion and the body portion is a hollow tube, which serves as the delivery channel. Further included in the hand piece is a nozzle that is placed at the first end of the body adjacent the delivery aperture. The nozzle has an opening for concentrating the abrasive as it passes through the nozzle. Further included is an optional nose tube, which is concentric with the delivery channel and the nozzle, and is placed adjacent the nozzle at the first end of the body. The tip mounts to the first end of the body and an anti-bleed seal is provided by an O-ring mounted on the first end of the body and engages with an inner-perimeter of the first end of the tip.

The waste debris collection device includes a waste can receiver, a waste canister, and a filter. The waste canister includes an intake port and return port. The intake port is coupled to the hand piece and the return port exits to ambient and includes a filter to prevent waste debris from being discharged to ambient. The waste canister typically is the same type of canister that is used initially to feed the abrasive to the feed chamber. The waste canister removably couples to the waste can receiver and a filter is fitted between the waste can receiver and the waste canister. The filter has a center intake port aperture in which the intake port passes, but the return path of the air drawn by vacuum passes through the filter, thus trapping the waste debris within the waste canister. A filter frame is used to support and retain the filter in position between the waste can receiver and the waste canister where the filter has substantially the same area as the opening of the waste canister. Pliable retention rings are used to secure the filter in place between the waste canister and the filter frame support.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF SPECIFIC EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 6, is not intended to limit the scope of the invention, as claimed, but is merely representative of the presently preferred embodiments of the invention.

The presently preferred embodiments of the invention will be best understood by reference to the drawings, wherein like parts are designated by like numerals throughout.

Figure 1:
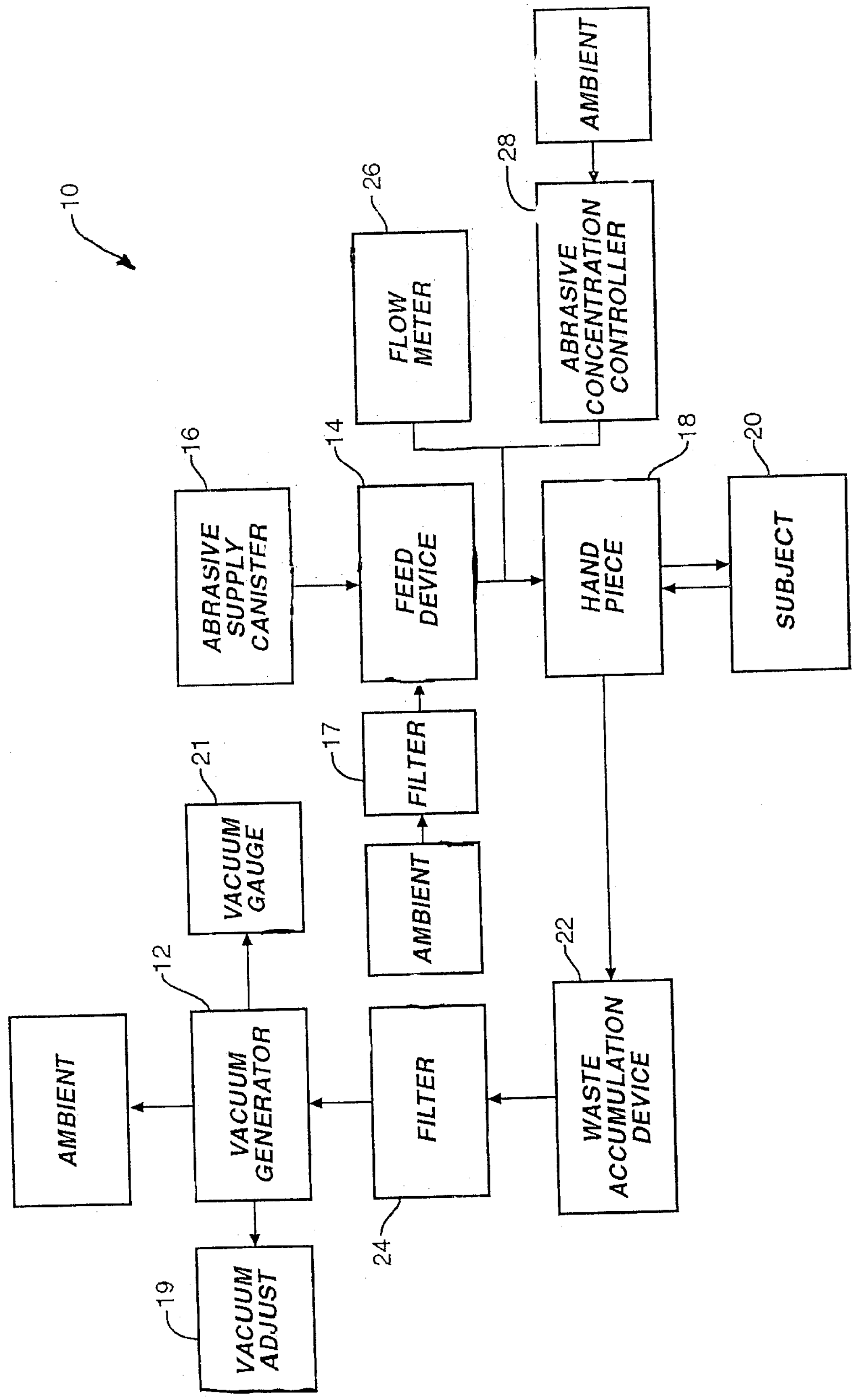
FIG. 1 depicts a schematic diagram of a dermabrasion system in accordance with the present invention.
Figure 2:
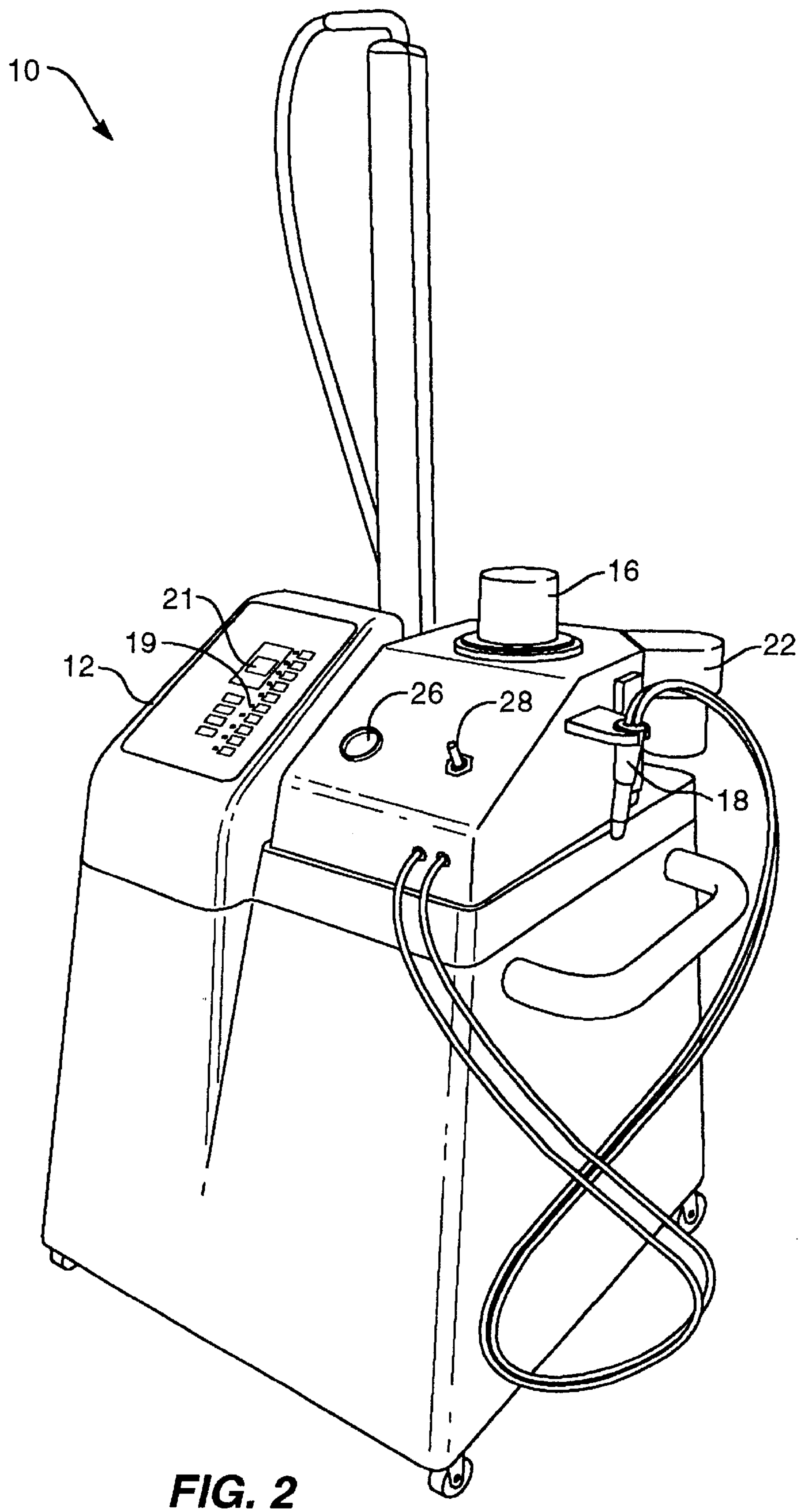
FIG. 2 illustrates a perspective view of the dermabrasion system in accordance with the present invention.

An abrasion system 10, which is optionally portable, is depicted in the block diagram of FIG. 1 as well as in FIG. 2. Dermabrasion apparatus 10 is a pneumatically driven apparatus that includes a vacuum generator 12. The pneumatic source may also be provided by a forced air system well known to those skilled in the art. Other pneumatic delivery systems will be readily apparent to those skilled in the art and should not be limited to solely a vacuum generator system or other forced air or compressed air delivery type arrangements. An airless pump may also be substituted as long as it provides adequate abrasive delivery and pick up though out the abrasion system.

Vacuum generator 12 also may be optionally coupled or decoupled from the remaining elements of the dermabrasion apparatus 10 and is not intended to be limited to only those dermabrasion systems that include self-contained pneumatic delivery systems. It is contemplated in one embodiment that apparatus 10 utilizes a vacuum generator such as that disclosed in commonly assigned U.S. patent application Ser. No. 09/309,958, filed May 11, 1999, incorporated by reference for all purposes. Further, since the dermabrasion apparatus 10 can utilize the vacuum generator 12 as disclosed in the cited patent application, it is possible to have both a dermabrasion apparatus and a massage or body contouring system.

Vacuum generator 12 couples to other elements within the system 10 via standard connection means. Vacuum generator 12 also vents to ambient during operation. A vacuum adjustment control 19 is provided with the generator to control the level of vacuum pressure generated thereby. The connection means can include metal or plastic tubing typically found in systems that are pneumatically operated.

The system 10 further includes an abrasive feed device 14 that couples to an abrasive supply canister 16 as well as to ambient. The ambient connection provides the needed air to deliver the abrasive from device 14 to the patient 20. A filter 17 is placed between the ambient source and feed device 14 to filter the incoming air supply as well as to prevent any abrasive within device 14 from exiting out the intake port from which ambient air is drawn. Both abrasive feed device 14 and abrasive supply canister 16 are shown in greater detail in FIG. 3. Filter 17 can be a sintered plastic, ceramic, or metallic filter that allows air to pass through, but not the abrasive. Other filters that can be utilized will be apparent to those skilled in the art such as membrane, fiber, and mesh filters, but are not limited solely to those named.

Abrasive feed device 14 further couples to a hand piece or wand 18, which is utilized to perform the dermabrasion on a patient or subject 20. The hand piece 18 provides both delivery of the abrasive material to the subject as well as retrieval of waste debris and abrasive during operation. This excess debris and material is deposited in waste collection device 22, which is also coupled to hand piece 18. A filter 24, such as another sintered or other suitable filter, serves to prevent any previously untrapped waste debris and abrasive from contaminating vacuum generator 12 or being vented to ambient, and is coupled between the waste collection canister 22 and vacuum generator 12. Waste collection or accumulation device 22 includes a filter (shown in FIG. 4B) that is used to prevent the vast majority of waste debris and abrasive from reaching filter 24 or vacuum generator 12.

Apparatus 10 includes a flow meter 26 and an abrasive concentration controller 28. Flow meter 26 displays the airflow generated within apparatus 10 so that the technician operating apparatus 10 can determine whether the airflow is sufficient for the procedure. Furthermore, flow meter 26 can also be used as a diagnostic device to determine if air flow within the system has fallen below acceptable levels due to clogging or fouling of filters. Should the technician need to adjust the airflow, the technician utilizes the vacuum level controller 19, which in this case is shown mounted on the control face of external vacuum generator 12.

Additionally, it may be desirable to vary the amount of abrasive in the air stream depending upon the nature of the procedure being performed. Toward this, the operator utilizes abrasive concentration controller 28 to mix ambient air into the abrasive-laden air coming from feed device 14 and leading toward hand piece 18. Flow meter 26 is well known to those skilled in the art and may be placed anywhere within the system where clean air flow occurs, i.e. before feed device 14 or after filter 24. In this example, the flow meter and concentration controller are both located proximate the hand piece.

Abrasive concentration controller 28 can be selected from a variety of controllers. For example, in one embodiment, the controller 28 is an infinitely adjustable rotary type that goes from full open to full close. It is the level of openess that determines the abrasive concentration in the system. Full open, which couples the hand piece to ambient and bleeds air into the system effectively reduces abrasive concentration to zero such that no abrasive is being delivered but that air flow and vacuum pressure remains unchanged.

Such a situation is advantageous for removing used abrasive and debris from the patient's skin, as is often desired at the end of a treatment. Conversely, full close maximizes abrasive concentration. A multi-position toggle switch may also be utilized that selects between full open, full close, or one or more levels in between.

Further still, both flow meter 26 and abrasive concentration controller 28 can be either manually adjustable or electrically or electronically adjustable, depending upon the types of gauge sensor and pressure adjustment means selected and implemented. Electronic control provides for greater precision in abrasive delivery and treatment consistency between treatment sessions.

A vacuum gauge 21 and vacuum pressure adjustment means 19 are found on vacuum generator 12 within apparatus 10. Gauge 21 and adjustment means 19 are well known in the art.

Figure 3:
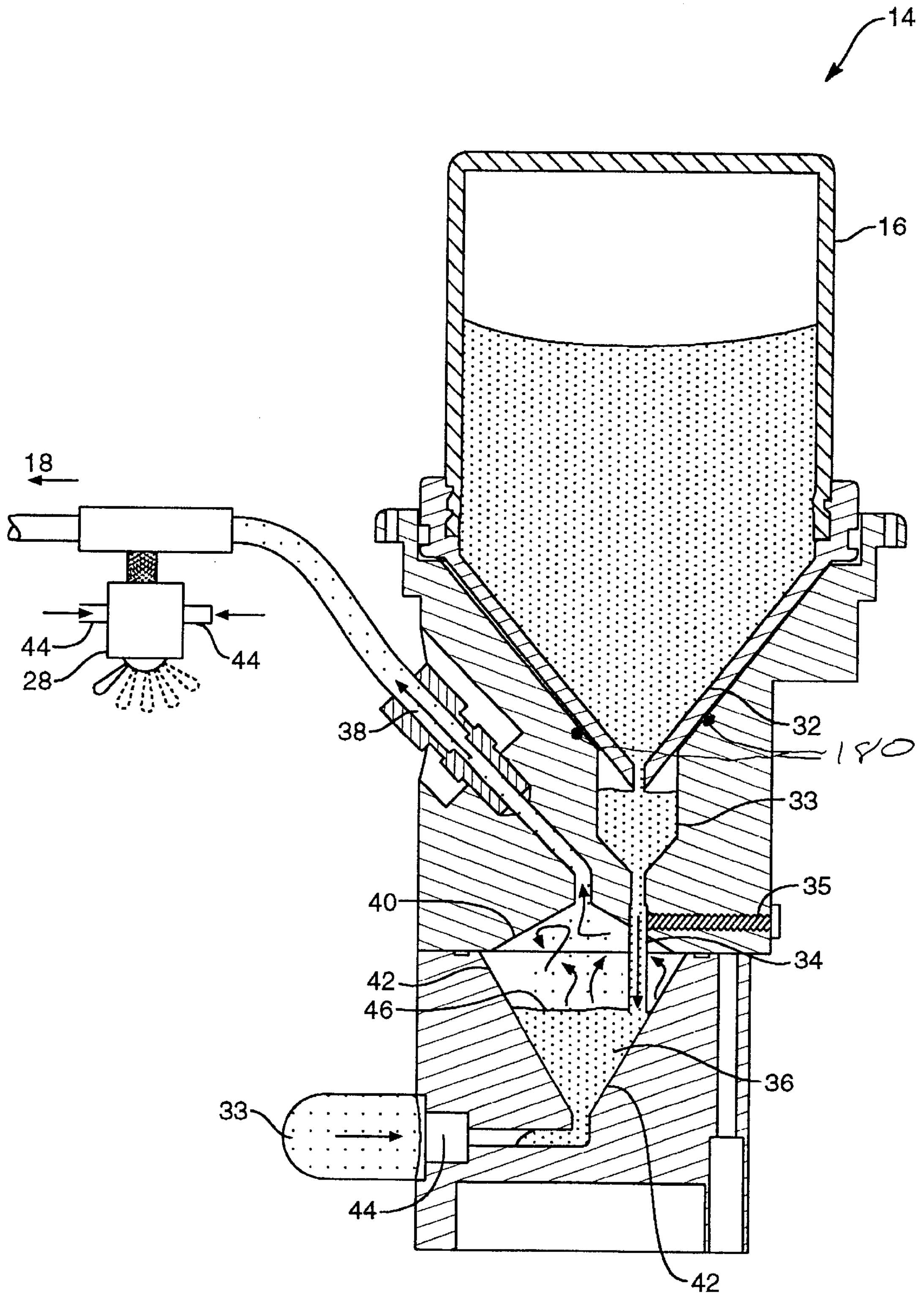
FIG. 3 illustrates the feeding device in accordance with principles of the present invention.

FIG. 3 illustrates the interaction of abrasive supply canister 16 with abrasive feeding device 14. Abrasive supply canister 16 further includes a funnel 30, which includes an aperture at the bottom tip to allow the abrasive stored therein to feed into abrasive feeding device 14. Abrasive supply canister 16 is typically a plastic or glass container having a threaded opening to which funnel 30 threads. A threaded cap (not shown) seals the canister 16 when it is does not have funnel 30 secured to it cr when it is not mated to feed device 14, such as during transportation or storage. Abrasive supply canister 16 holds approximately one pound of abrasive material, but can hold more or less material in alternative embodiments. The abrasive material is selected from known particulate abrasives, such as aluminum oxide or other organic or inorganic micro-abrasive known to those skilled in the art.

Once the funnel 30 is placed on abrasive canister device 16, it is inverted so that the abrasive material is gravity fed within a holding chamber 32, which has a shape conforming to that of funnel 30. A transition chamber 33 is positioned between holding chamber 32 and feed tube 34. An arrow pointing downward shows the gravity feed direction of the abrasive material found in canister 16. The abrasive continues its gravity fall through feed tube 34, which has a defined length that extends within a feeding chamber 36. Further, feed tube 34 can be varied in length by control device 35 that raises or lowers tube 34 within chamber 36. This allows the operator to refine the abrasive flow within the system 10 by controlling the amount of abrasive that is allowed into chamber 36 during operation. Alternately, feed tube 34 can be of a predefined length which is fixed to the bottom of transition chamber 33 should adjustability not be required. Feed tube 34 can be substantially vertical or even angled to some degree so as not to interfere with the walls of feeding chamber 36. Optionally, the end of tube 34 is cut so as to be substantially horizontal in either configuration.

In alternative embodiments, feeding device 16 can include a vibrating motor that gently sifts the abrasive into feeding chamber 36. Further still, canister 16 can be mated to a feed tube that connects to tube 34 with the canister being suspended allowing the abrasive to gravity feed to chamber 36. The funnel 30 might then be mounted to a gimble mechanism or other rotational mechanism which would allow the canister to be mated to it in a substantially upright position and then rotated to an inverted position to thereupon allow gravity-feed of the abrasive via the connecting feed tube.

Feeding chamber 36 is illustrated to have a cone shape having an arc ranging from 40 degrees to 90 degrees, with 60 degrees being preferred. This is but one embodiment and other configurations are possible. For example, chamber 36 can have an inverted pyramid shape, a bowl shape, a cylindrical shape, or a combination of these geometries so long as the abrasive lofts sufficiently to provide uniform and consistent abrasive flow out of feeding chamber 36. Likewise, the shape of holding chamber 32 can be any of these types of geometries so long as the abrasive feeds to feeding chamber 36 uniformly and consistently without waste or clogging.

One end of feed tube 34 extends into lofting chamber 36. The bottom end of feed tube 34 limits the amount of abrasive that can be held within chamber 36. This limit is shown by line 46. It is by controlling of the amount of abrasive material within feeding chamber 36 that improves the delivery of a uniform and consistent supply of abrasive to hand wand 18 during operation. The abrasive material is lofted in the chamber during operation before exiting through transport tube 38. Transport tube 38 further couples to hand wand 18 for delivery of the abrasive material to the subject 20. In this embodiment, a vacuum is drawn on transport tube 38 with an ambient air source coming in through port 44. The ambient air passes through filter 33 into the bottom of feeding chamber 36. As the vacuum forms within feeding chamber 36, air is effectively bubbled through the abrasive pile and the abrasive particles are thereupon lofted and directed towards tube 38 via a feed funnel 40 formed in the top of feeding chamber 36. Feed funnel 40 has an arc of greater than 90 degrees with an aperture into tube 38. Funnel 40 serves to feed the lofted abrasive material through tube 38 to hand piece 18 during operation. The sloped side walls 42 of feeding chamber 36 serve to enhance the uniform delivery of abrasive material even while the contents of abrasive supply canister 16 empty completely into feeding chamber 36. The remaining arrows within feeding chamber 36 illustrate the physical action of the abrasive material during the operation of apparatus 10 as well as the final direction through tube 38 as the abrasive material is carried to hand piece 18.

An ambient port 44 is coupled between tube 38 and hand piece 18 and includes a variable open/close device that functions as controller 28 to control the amount of air bled into the abrasive stream during operation, thereby controlling the concentration of abrasive delivered to hand piece 18. In an alternative embodiment, the height of funnel 40 relative to feeding chamber 36 can be increased or decreased to change the abrasive feed characteristics according to the technician's preference.

Abrasive feeding device 14 is typically made from a durable material, such as aluminum, stainless steel, or high durability plastic material. Device 14 can also be made from other materials as long as they are inert to the abrasive and durable for operation.

Figure 4A:
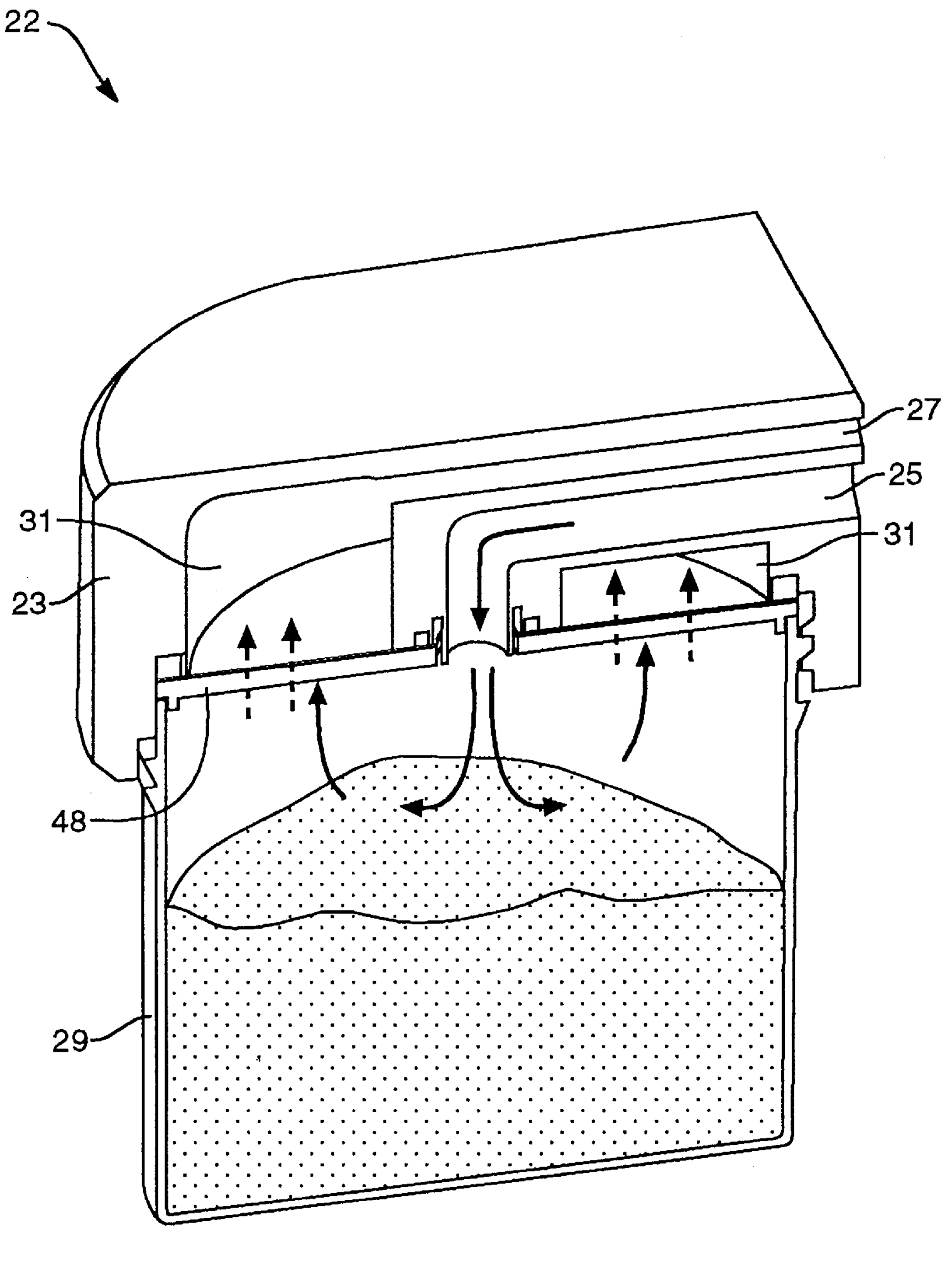
FIG. 4A illustrates a collection device utilized to hold waste debris after the abrading procedure in accordance with the present invention.

The abrasive within feeding chamber 36 then is directed through hand piece 18 to perform the desired abrasive operation on subject 20. During the actual abrading procedure, the abrasive abrades the skin causing waste debris and refuse that must be removed so as not to interfere with or contaminate the abraded surface. The pneumatic air supply, in this case vacuum generator 12, provides a vacuum in hand piece 18 that draws the waste refuse and debris away from the subject while at the same time performing surface abrasion. The waste refuse collects in abrasive collection device 22. Abrasive collection device 22 is shown in FIG. 4A, which is a cut-away perspective view of the abrasive collection device 22.

Collection device 22 includes a waste can receiver 23, which has an intake port 25 and a return port 27, a waste canister 29, and a filter 48. Waste can receiver 23 has a threaded seal in which to receive canister 29. Canister 29 collects the waste refuse during an abrasion procedure for later disposal. In the preferred embodiment, Canister 29 is identical to canister 16 used to feed the abrasive; however, this might not be the case in other embodiments. Once canister 16 is empty, it is removed and used to replace canister 29 once it is f full, which is usually by the time canister 16 is empty. A cap threads onto canister 29 once it is full to seal the contents for proper disposal and to minimize any unnecessary contact with the refuse by the technician.

The waste refuse travels through intake port 25 to be deposited into canister 29. The air flows through filter 48 before exiting through return port 27, which couples to second filter 24 before being dispersed to ambient air. Although not mandatory for operation, use of second filter 24 is recommended to both remove any material untrapped by filter 48 and to act as a fail-safe particulate trap in the event filter 48 is either inadvertently left out of the system or is improperly installed. A return cavity 31 is disposed between filter 48 and return port 27 to keep the airflow from being unduly restricted during the filtering procedure.

Figure 4B:
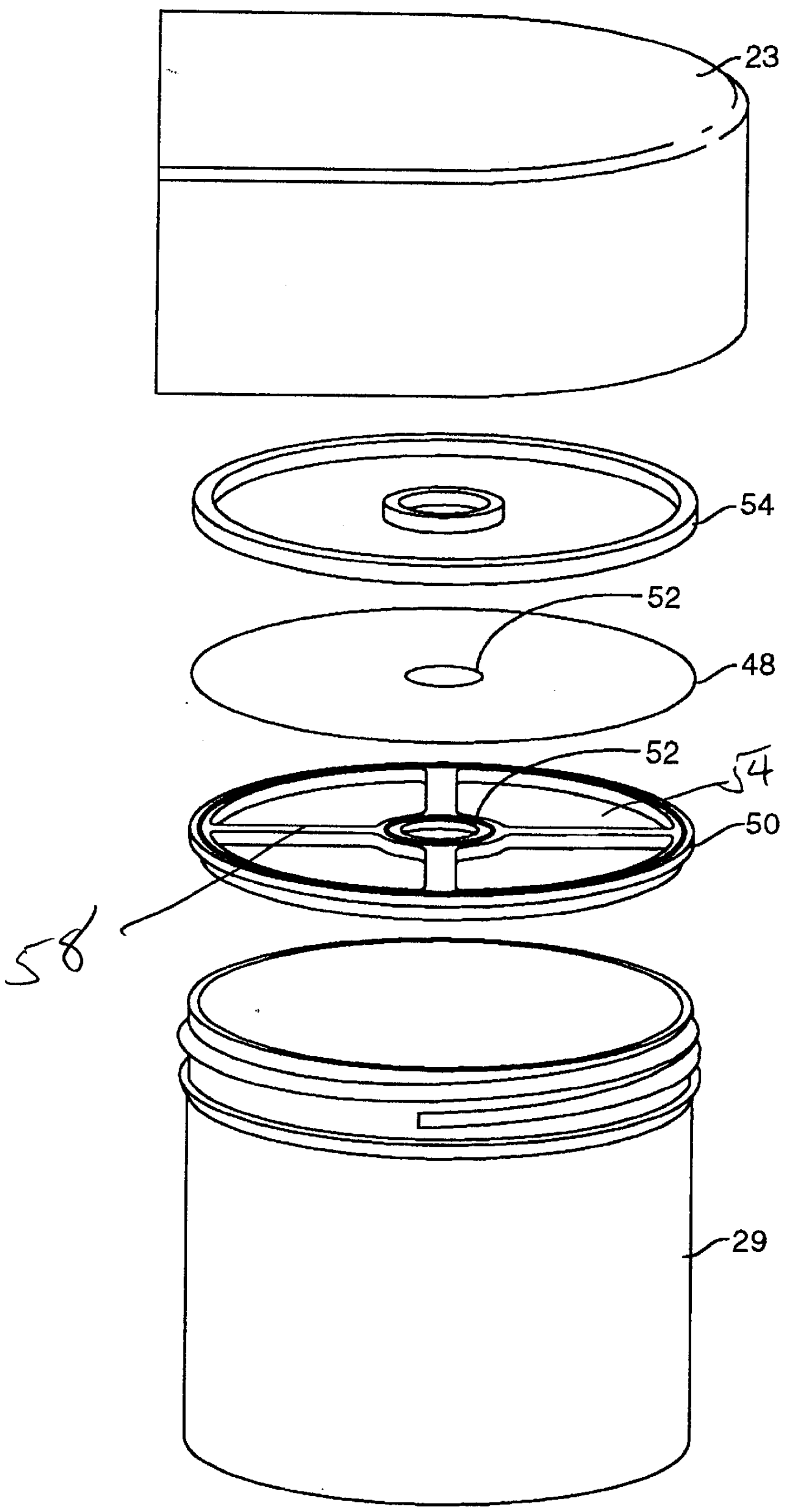
FIG. 4B depicts an exploded view of the collection device of FIG. 4A accordance with the present invention.

Referring to FIG. 4B, Filter 48 includes a support element 50, an intake aperture 52, through which the waste refuse material passes into canister 29, and filter apertures 54. The waste refuse material passes through aperture 52 into canister 29. The vacuum within device 22 then passes through filter 48 and underlying filter apertures 54, filter 48 preventing the refuse material from passing to chamber 31 to the vacuum generator 12.

Ring seals 54 are positioned within receiver 23 and superior to filter 48 about both its outer perimeter and its inner perimeter about aperture 52 to provide compliant sealing surfaces. Additionally, inner and outer crimping features 58 are provided upon the top surface of support element 50 and are positioned beneath ring seals 54. The crimping features 58 can be a one or a series of adjacent concentric ridges that press into filter 48 to hold it in place against compliant ring seals 54 and to provide an anti-bleed seal.

Filter 48 provides a larger surface area than filters utilized in the collection of the waste debris of the prior art. Further, the surface area is also such that the airflow is not inhibited since air flow return port 27 is removed from being immediately adjacent the filter 48. Also, in one embodiment filter 48 is disposable and inexpensive so it can be replaced between treatments, thus eliminating the progressive clogging experienced with durable-use filters or cleaning steps typically required in the prior art.

It is also intended that the discharge tube between hand piece 18 and waste collection or accumulation device 22 be easily removable so that it can be cleaned between sessions to prevent contamination and unsanitary build up of the waste debris residue that remains in the tube. Each end of the discharge tube can be pressure fitted or coupled via connectors that provide a suitable vacuum seal to prevent air bleeding into the system and lowering airflow inadvertently.

Figure 5A:
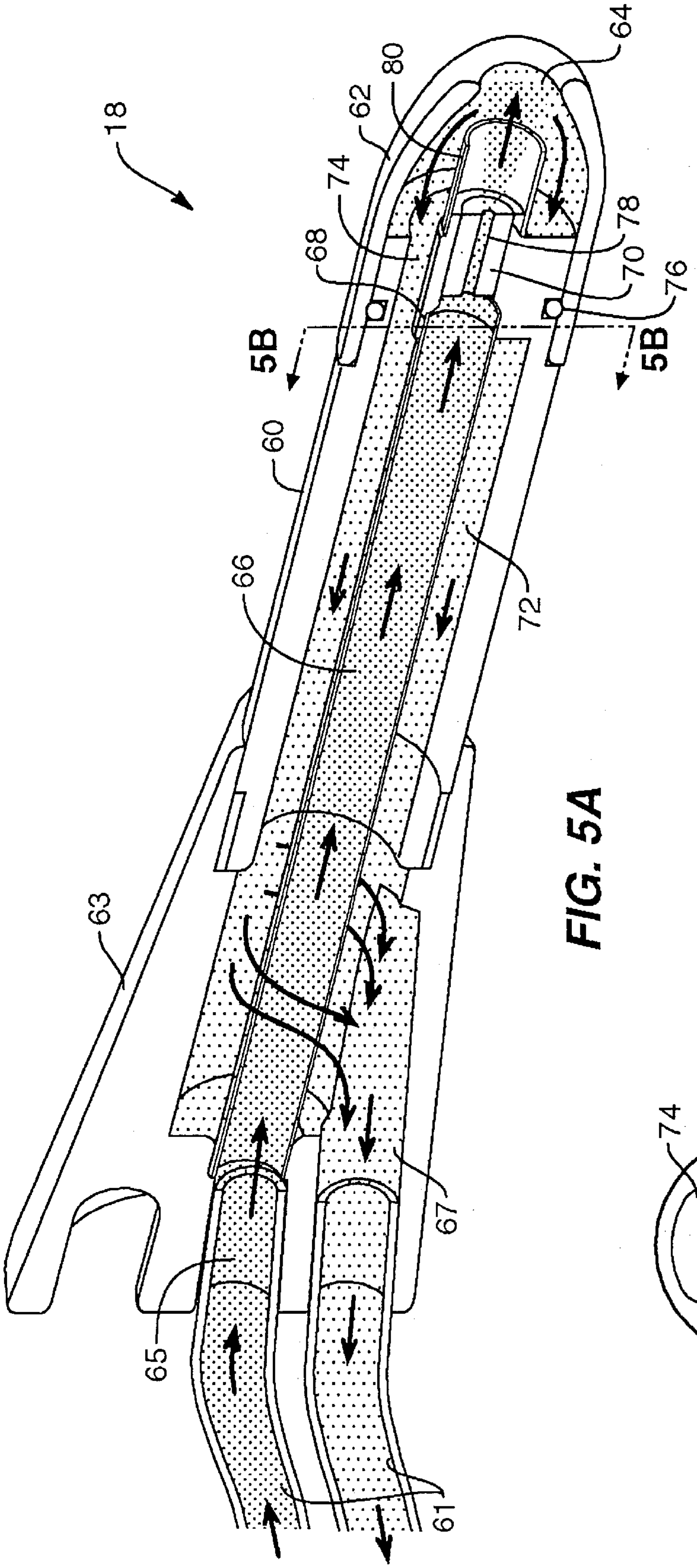
FIG. 5A illustrates a cross-sectional perspective view the hand piece utilized with the dermabrasion apparatus of FIG. 2 in accordance with the present invention.
Figure 5B:
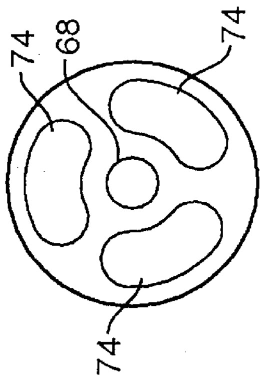
FIG. 5B illustrates a cross-sectional view along the 5B direction in FIG. 5A.

Hand piece 18 is shown in cross-sectional detail in FIG. 5A, which is a cross-sectional perspective view along the longitudinal center axis. Hand piece 18 is assembled in a plurality of parts. There are three main portions assembled from these parts, which include hand piece body 60, tip 62, and end portion 63. Tip 62 friction mates with one end of hand piece body 60, while the other end of hand piece body 60 couples to end portion 63. End portion 63 is flared shaped for operator comfort during an abrasion session and so it will be retained in a retaining member on the vacuum apparatus 12 of FIG. 2. End portion 63 has two apertures, a supply aperture 65 and a return aperture 67. The supply aperture 65 couples to feeding device 14 to receive the abrasive for the treatment. The return aperture 67 couples to the waste collection device 22. Plastic flexible tubes 61 are used in one embodiment where the tubes have a slightly greater diameter than the apertures so that they friction fit there in and extend at least ½" to provide an adequate barrier from air bleed at these connection points.

A center channel 66 is positioned within a recess of end portion 65 to connect with the supply aperture 65. Center channel 66 fits within body 62 until it engages an output aperture 68. Within the output aperture 68 is fitted a nozzle 70 that concentrates the abrasive just prior to abrading a selected surface and causes the abrasive to stream in a fan cone pattern, but with a tight radius for control. Surrounding center channel 66 is a return channel 72, which is larger than and concentric with channel 66. The larger diameter of channel 68 allows for a sufficient air flow that the waste debris is readily transported to the refuse accumulation device 22 without clogging or hindering the air flow of the supply abrasive. Surrounding aperture 68 are a plurality of intake apertures 74. The intake apertures open to channel 68 and allow the waste debris to be removed from within tip 62 during treatment.

Tip 62 is generally bell-shaped and includes an abrasive aperture 64. Abrasive aperture 64 contacts the surface to be treated arid closes the pneumatic circuit to draw abrasive through the system and abrade the surface. Abrasive aperture 64 is approximately one-quarter inch in diameter and is applied to the subject, such as a patient's skin, during the abrasive procedure. An O-ring 76 is fitted within a groove 74 about the end of body 60 to which tip 62 fits. O-ring 76 serves to proved a tight seal against air-bleed within the airflow. The O-ring 76 is flexible and pliant, typically made from rubber, neoprene, silicone, plastic, or any like and compatible substance.

Nozzle 70 is generally cylindrical in shape with an aperture 78 along its center axis. Nozzle 70 is made of a hard, durable substance that withstands the abrading process of the abrasive as the abrasive hits the nozzle with full force. These materials can comprise, but are not limited to, stainless steel, ceramic, aluminum, tungsten carbide, and other comparable substances. A nose tube 80 is optionally mounted to the operational end of body 60 and is concentric with nozzle 70. Nose tube 80 is generally cylindrical and helps divert the waste debris away from the abrasive during an abrading procedure while protecting the incoming abrasive steam from flow aberrations.

Since the hand piece 18 can be readily disassembled, it can be taken apart and thoroughly cleaned to avoid contamination and other health risks possible in performing dermabrasion and removing the waste debris. Further, the parts to hand piece 18 can be made of inexpensive, yet durable materials that allow for the hand piece, in part or in total, to be disposable.

The jet path of the abrasive may fans out enough to strike the inner wall of tip 62 at the margins of aperture 69. Since the abrasive is traveling at a high rate of speed, it causes the inner wall of tip 62 to wear away. Additionally, the act of scanning tip 62 across abrasive-covered skin will serve to abrade the outer surface of tip 62 near aperture 69. Accordingly, tip 62 is made compact and inexpensive so that it can be easily replaced and disposed of, preferably after each treatment. Suitable materials used to make tip 62 include polycarbonate, other plastics and resins, and other suitable substances with similar properties, specifically high-speed/low-cost moldability.

The present invention may be embodied in other specific forms without departing from its spirit or essential characteristics. The described embodiments are to be considered in all respects only as illustrative and not restrictive. For example, the abrasion system can be scaled to other commercial and industrial uses such as sand blasting. deposition delivery to a surface, and is not intended to be limited to just dermabrasion systems as disclosed. The scope of the invention is, therefore, indicated by the appended claims, rather than by the foregoing description. All changes which come within the meaning and range of equivalency of the claims are to be embraced within their scope.

What is claimed is:

1. An abrasive handling device for use in an abrasion apparatus, comprising:

a feeding chamber that has generally funnel-shaped portion that receives an abrasive;

a receiving channel that limits the amount of abrasive supplied to the feeding chamber;

an intake aperture, connected to a base of the feeding chamber to receive means for displacing the abrasive in a substantially vertical direction; and a delivery channel, placed above the feeding chamber to receive the displaced abrasive.

2. The device according to claim 1 further comprising a generally funnel-shaped supply device, positioned above the feeding chamber and connected to the receiving channel.

3. The device according to claim 2 further comprising an abrading material holding container removably fitted with a funnel that fits within the supply device.

4. The device according to claim 1 wherein the device is pneumatically driven.

5. The device according to claim 1 wherein the funnel-shape of the lofting chamber forms an arc ranging approximately 40 degrees to 90 degrees.

6. The device according to claim 1 wherein the funnel-shape of the feeding chamber forms an arc of generally 60 degrees.

7. The device according to claim 4 further comprising an airflow regulator, coupled to the delivery channel, to regulate the flow abrasive during operation.

8. The device according to claim 1 wherein the delivery channel comprises an inverted funnel-shaped opening within the feeding chamber.

9. The device according to claim 1 further comprising a transition chamber disposed between the supply device and the feeding chamber.

10. The device according to claim 1, wherein the receiving channel extends within the feeding chamber a sufficient distance to control the amount of abrasive filling the feeding chamber.

11. The device according to claim 1, further comprising:

a hand piece coupled to the abrasive handling device; and a waste retrieval holding device, coupled to the hand piece, to collect and store the abrasive and waste debris after treatment.

12. The device according to claim 11, wherein the waste retrieval holding device comprises a filter.

13. The device according to claim 12, wherein the filter comprises a fabric having pores sufficiently small to prevent the abrasive and collected waste from passing therethrough.

14. The device according to claim 12, wherein the filter is removable.

15. The device according to claim 12, wherein the waste retrieval holding device further comprises:

a waste can receiver having an intake port and a return port; and a waste canister removably coupled to the waste can receiver at an open end of the waste canister.

16. The device according to claim 11, wherein the hand piece comprises a supply aperture and a return aperture.

17. The device according to claim 11, wherein the hand piece comprises a removable tip that has an aperture that contacts the surface to be abraded.

18. The device according to claim 2, wherein the supply device utilizes gravity to feed the abrasive to the feeding chamber.

19. The device according to claim 4, wherein a motor coupled to the abrasive handling device pneumatically drives the device.

20. The device according to claim 19, wherein the motor generates a vacuum for drawing the abrasive through the device.

21. The abrasive handling device according to claim 20, further comprising:

a delivery and retrieval hand piece coupled to the abrasive handing device;

a waste debris receiving device, coupled to the hand piece, to collect and store waste debris and the derm-abrasive after treatment; and a massage device coupled to and operable by the motor, comprising:

a head having a concave inner wall and a rim, the concave wall defining an orifice communicating with a vacuum source and the rim having a substantially flat contact surface, the concave wall and rim defining a cavity and an opening to the cavity, the cavity being substantially semi-spherical;

a post extending from the concave inner wall toward the opening, the post being slightly recessed within the cavity and having a substantially flat contact surface, the post being substantially vertically cylindrical; and a handle defining an internal conduit, the conduit having a first open end and a second open end, the conduit communicating with the orifice at the first open end and communicating with the vacuum source at the second open end.

* * * * *

UNITED STATES PATENT AND TRADEMARK OFFICE

CERTIFICATE OF CORRECTION

PATENT NO. : 6,582,442 B2 
DATED : June 24, 2003
INVENTOR(S) : Eric M. Simon and Randall D. Block It is certified that error appears in the above-identified patent and that said Letters Patent is hereby corrected as shown below:

Column 8,
Line 47, delete "f"

Column 10,
Line 1, delete "arid", insert -- and --

Signed and Sealed this

Seventh Day of October, 2003

JAMES E. ROGAN
*Director of the United States Patent and Trademark Office*